United States Patent
Lunsford et al.

(10) Patent No.: US 9,364,259 B2
(45) Date of Patent: Jun. 14, 2016

(54) SYSTEM AND METHOD FOR DELIVERING EXPANDING TROCAR THROUGH A SHEATH

(75) Inventors: John Lunsford, San Carlos, CA (US);
Fiona Sander, Los Altos, CA (US);
Hoang Phan, Fremont, CA (US)

(73) Assignee: Xlumena, Inc., Mountain View, CA (US)

(*) Notice: Subject to any disclaimer, the term of this patent is extended or adjusted under 35 U.S.C. 154(b) by 759 days.

(21) Appl. No.: 12/757,408

(22) Filed: Apr. 9, 2010

(65) Prior Publication Data
US 2010/0268175 A1 Oct. 21, 2010

Related U.S. Application Data

(60) Provisional application No. 61/171,228, filed on Apr. 21, 2009.

(51) Int. Cl.
| | |
|---|---|
| *A61M 5/32* | (2006.01) |
| *A61B 17/34* | (2006.01) |
| *A61B 17/32* | (2006.01) |
| *A61B 17/3207* | (2006.01) |
| *A61B 17/3209* | (2006.01) |
| *A61B 17/00* | (2006.01) |

(52) U.S. Cl.
CPC ......... *A61B 17/3478* (2013.01); *A61B 17/3209* (2013.01); *A61B 17/320016* (2013.01); *A61B 17/320725* (2013.01); *A61B 2017/00278* (2013.01); *A61B 2017/346* (2013.01)

(58) Field of Classification Search
CPC ................... A61B 17/3478; A61B 17/320725; A61B 17/320016; A61B 17/3209; A61B 2017/346; A61B 2017/00278
USPC .................. 606/185, 41, 167, 170, 171, 181; 604/96.01, 272, 164.01, 164.03; 600/115, 106; 27/24.1
See application file for complete search history.

(56) References Cited

U.S. PATENT DOCUMENTS

| | | |
|---|---|---|
| 2,127,903 A | 8/1938 | Bowen |
| 3,039,468 A | 6/1962 | Price |
| 3,717,151 A | 2/1973 | Collett |
| 3,874,388 A | 4/1975 | King et al. |
| 3,970,090 A | 7/1976 | Loiacono |

(Continued)

FOREIGN PATENT DOCUMENTS

| | | |
|---|---|---|
| DE | 102006050385 | 4/2008 |
| EP | 637431 A1 | 2/1995 |

(Continued)

OTHER PUBLICATIONS

International Search Report and Written Opinion of PCT Application No. PCT/US2010/031612, mailed Jun. 18, 2010, 8 pages total.

(Continued)

*Primary Examiner* — Tuan V Nguyen
*Assistant Examiner* — Tin Nguyen

(57) ABSTRACT

A trocar has an elongate body and a tissue-penetrating tip. One or more radially extending blade(s) are provided near the tissue-penetrating tip of the trocar body so that they automatically open as the trocar is advanced through tissue. The blades will enlarge the penetration which was formed by the tip of the trocar.

13 Claims, 6 Drawing Sheets

(56) References Cited

U.S. PATENT DOCUMENTS

| | | | |
|---|---|---|---|
| 4,173,392 A | 11/1979 | Ekinaka et al. | |
| 4,235,238 A | 11/1980 | Ogiu et al. | |
| 4,580,568 A | 4/1986 | Gianturco | |
| 4,587,972 A | 5/1986 | Morantte, Jr. | |
| 4,608,965 A | 9/1986 | Anspach, Jr. et al. | |
| 4,610,242 A | 9/1986 | Santangelo et al. | |
| 4,705,040 A | 11/1987 | Mueller et al. | |
| 4,790,813 A | 12/1988 | Kensey | |
| 4,869,263 A | 9/1989 | Segal et al. | |
| 4,896,678 A | 1/1990 | Ogawa | |
| 4,917,097 A | 4/1990 | Proudian et al. | |
| 4,920,967 A | 5/1990 | Cottonaro et al. | |
| 4,950,285 A | 8/1990 | Wilk | |
| 4,973,317 A | 11/1990 | Bobrove | |
| 4,990,139 A | 2/1991 | Jang | |
| 5,024,655 A | 6/1991 | Freeman et al. | |
| 5,061,275 A | 10/1991 | Wallsten et al. | |
| 5,064,435 A | 11/1991 | Porter | |
| 5,180,392 A | 1/1993 | Skeie et al. | |
| 5,183,464 A | 2/1993 | Dubrul et al. | |
| 5,197,971 A | 3/1993 | Bonutti | |
| 5,207,229 A | 5/1993 | Winters | |
| 5,209,727 A | 5/1993 | Radisch, Jr. et al. | |
| 5,211,651 A | 5/1993 | Reger et al. | |
| 5,221,258 A | 6/1993 | Shturman | |
| 5,224,945 A | 7/1993 | Pannek, Jr. | |
| 5,226,421 A | 7/1993 | Frisbie et al. | |
| 5,234,447 A | 8/1993 | Kaster et al. | |
| 5,246,007 A | 9/1993 | Frisbie et al. | |
| 5,257,990 A | 11/1993 | Nash | |
| 5,258,000 A | 11/1993 | Gianturco | |
| 5,261,920 A | 11/1993 | Main et al. | |
| 5,275,610 A | 1/1994 | Eberbach | |
| 5,275,611 A | 1/1994 | Behl | |
| 5,282,824 A | 2/1994 | Gianturco | |
| 5,290,249 A | 3/1994 | Foster et al. | |
| 5,304,198 A | 4/1994 | Samson | |
| 5,330,497 A | 7/1994 | Freitas et al. | |
| 5,353,785 A | 10/1994 | Wilk | |
| 5,368,595 A | 11/1994 | Lewis | |
| 5,372,588 A | 12/1994 | Farley et al. | |
| 5,381,788 A * | 1/1995 | Matula et al. | 600/214 |
| 5,387,235 A | 2/1995 | Chuter | |
| 5,395,349 A | 3/1995 | Quiachon et al. | |
| 5,425,739 A | 6/1995 | Jessen | |
| 5,443,484 A | 8/1995 | Kirsch et al. | |
| 5,458,131 A | 10/1995 | Wilk | |
| 5,462,561 A | 10/1995 | Voda | |
| 5,470,337 A | 11/1995 | Moss | |
| 5,489,256 A | 2/1996 | Adair | |
| 5,495,851 A | 3/1996 | Dill et al. | |
| 5,496,311 A | 3/1996 | Abele et al. | |
| 5,520,700 A | 5/1996 | Beyar et al. | |
| 5,531,699 A | 7/1996 | Tomba et al. | |
| 5,536,248 A | 7/1996 | Weaver et al. | |
| 5,588,432 A | 12/1996 | Crowley | |
| 5,601,588 A | 2/1997 | Tonomura et al. | |
| 5,603,698 A | 2/1997 | Roberts et al. | |
| 5,620,456 A | 4/1997 | Sauer et al. | |
| 5,620,457 A | 4/1997 | Pinchasik et al. | |
| 5,632,717 A | 5/1997 | Yoon | |
| 5,662,664 A | 9/1997 | Gordon et al. | |
| 5,688,247 A | 11/1997 | Haindl et al. | |
| 5,697,944 A | 12/1997 | Lary | |
| 5,709,671 A | 1/1998 | Stephens et al. | |
| 5,709,707 A | 1/1998 | Lock et al. | |
| 5,713,870 A | 2/1998 | Yoon | |
| 5,713,874 A | 2/1998 | Ferber | |
| 5,725,552 A | 3/1998 | Kotula et al. | |
| 5,797,906 A | 8/1998 | Rhum et al. | |
| 5,817,062 A | 10/1998 | Flom et al. | |
| 5,827,276 A | 10/1998 | LeVeen et al. | |
| 5,830,222 A | 11/1998 | Makower | |
| 5,843,050 A | 12/1998 | Jones et al. | |
| 5,843,116 A | 12/1998 | Crocker et al. | |
| 5,843,127 A | 12/1998 | Li | |
| 5,853,421 A | 12/1998 | Leschinsky et al. | |
| 5,853,422 A | 12/1998 | Huebsch et al. | |
| 5,855,576 A | 1/1999 | LeVeen et al. | |
| 5,857,999 A | 1/1999 | Quick et al. | |
| 5,858,006 A | 1/1999 | Van der Aa et al. | |
| 5,882,340 A | 3/1999 | Yoon | |
| 5,893,856 A | 4/1999 | Jacob et al. | |
| 5,897,567 A | 4/1999 | Ressemann et al. | |
| 5,935,107 A | 8/1999 | Taylor et al. | |
| 5,944,738 A | 8/1999 | Amplatz et al. | |
| 5,951,576 A | 9/1999 | Wakabayashi | |
| 5,951,588 A | 9/1999 | Moenning | |
| 5,957,363 A | 9/1999 | Heck | |
| 5,993,447 A | 11/1999 | Blewett et al. | |
| 6,007,522 A | 12/1999 | Agro et al. | |
| 6,007,544 A | 12/1999 | Kim | |
| 6,015,431 A | 1/2000 | Thornton et al. | |
| 6,017,352 A | 1/2000 | Nash et al. | |
| 6,022,359 A | 2/2000 | Frantzen | |
| 6,036,698 A * | 3/2000 | Fawzi et al. | 606/114 |
| 6,074,416 A | 6/2000 | Berg et al. | |
| 6,080,174 A | 6/2000 | Dubrul et al. | |
| 6,099,547 A | 8/2000 | Gellman et al. | |
| 6,113,609 A | 9/2000 | Adams | |
| 6,113,611 A | 9/2000 | Allen et al. | |
| 6,190,353 B1 | 2/2001 | Makower et al. | |
| 6,228,039 B1 | 5/2001 | Binmoeller | |
| 6,231,515 B1 | 5/2001 | Moore et al. | |
| 6,231,587 B1 | 5/2001 | Makower | |
| 6,241,757 B1 | 6/2001 | An et al. | |
| 6,241,758 B1 | 6/2001 | Cox | |
| 6,251,084 B1 | 6/2001 | Coelho | |
| 6,264,675 B1 | 7/2001 | Brotz | |
| 6,277,137 B1 | 8/2001 | Chin | |
| 6,290,485 B1 | 9/2001 | Wang | |
| 6,309,415 B1 | 10/2001 | Pulnev et al. | |
| 6,319,272 B1 | 11/2001 | Brenneman et al. | |
| 6,322,495 B1 | 11/2001 | Snow et al. | |
| 6,325,798 B1 | 12/2001 | Edwards et al. | |
| 6,334,446 B1 | 1/2002 | Beyar | |
| 6,348,064 B1 | 2/2002 | Kanner | |
| 6,358,264 B2 | 3/2002 | Banko | |
| 6,371,964 B1 | 4/2002 | Vargas et al. | |
| 6,371,965 B2 | 4/2002 | Gifford et al. | |
| 6,391,036 B1 | 5/2002 | Berg et al. | |
| 6,402,770 B1 | 6/2002 | Jessen | |
| 6,432,040 B1 | 8/2002 | Meah | |
| 6,436,119 B1 | 8/2002 | Erb et al. | |
| 6,447,524 B1 | 9/2002 | Knodel et al. | |
| 6,454,765 B1 | 9/2002 | LeVeen et al. | |
| 6,475,168 B1 | 11/2002 | Pugsley, Jr. et al. | |
| 6,475,185 B1 | 11/2002 | Rauker et al. | |
| 6,475,222 B1 | 11/2002 | Berg et al. | |
| 6,485,496 B1 | 11/2002 | Suyker et al. | |
| 6,488,653 B1 | 12/2002 | Lombardo | |
| 6,503,247 B2 | 1/2003 | Swartz et al. | |
| 6,508,252 B1 | 1/2003 | Berg et al. | |
| 6,520,908 B1 | 2/2003 | Ikeda et al. | |
| 6,535,764 B2 | 3/2003 | Imran et al. | |
| 6,540,670 B1 | 4/2003 | Hirata et al. | |
| 6,547,776 B1 | 4/2003 | Gaiser et al. | |
| 6,575,967 B1 | 6/2003 | LeVeen et al. | |
| 6,610,100 B2 | 8/2003 | Phelps et al. | |
| 6,614,595 B2 | 9/2003 | Igarashi | |
| 6,616,675 B1 | 9/2003 | Evard et al. | |
| 6,620,122 B2 | 9/2003 | Stinson et al. | |
| 6,626,917 B1 | 9/2003 | Craig | |
| 6,626,919 B1 | 9/2003 | Swanstrom | |
| 6,632,197 B2 | 10/2003 | Lyon | |
| 6,635,068 B1 | 10/2003 | Dubrul et al. | |
| 6,638,213 B2 | 10/2003 | Ogura et al. | |
| 6,645,205 B2 | 11/2003 | Ginn | |
| 6,656,182 B1 | 12/2003 | Hayhurst | |
| 6,656,206 B2 | 12/2003 | Corcoran et al. | |
| 6,669,708 B1 | 12/2003 | Nissenbaum et al. | |
| 6,682,536 B2 | 1/2004 | Vardi et al. | |
| 6,712,757 B2 | 3/2004 | Becker et al. | |
| 6,736,828 B1 | 5/2004 | Adams et al. | |

(56) References Cited

U.S. PATENT DOCUMENTS

| | | |
|---|---|---|
| 6,746,472 B2 | 6/2004 | Frazier et al. |
| 6,746,489 B2 | 6/2004 | Dua et al. |
| 6,749,621 B2 | 6/2004 | Pantages et al. |
| 6,752,965 B2 | 6/2004 | Levy |
| 6,773,440 B2 | 8/2004 | Gannoe et al. |
| 6,835,189 B2 | 12/2004 | Musbach et al. |
| 6,902,535 B2 | 6/2005 | Eberhart et al. |
| 6,916,332 B2 | 7/2005 | Adams |
| 6,921,361 B2 | 7/2005 | Suzuki et al. |
| 6,921,387 B2 | 7/2005 | Camrud |
| 6,942,678 B2 | 9/2005 | Bonnette et al. |
| 6,960,233 B1 | 11/2005 | Berg et al. |
| 6,966,917 B1 | 11/2005 | Suyker et al. |
| 6,974,467 B1 | 12/2005 | Gonzales, Jr. |
| 6,979,290 B2 | 12/2005 | Mourlas et al. |
| 7,018,401 B1 | 3/2006 | Hyodoh et al. |
| 7,056,325 B1 | 6/2006 | Makower et al. |
| 7,077,850 B2 | 7/2006 | Kortenbach |
| 7,131,948 B2 | 11/2006 | Yock |
| 7,134,438 B2 | 11/2006 | Makower et al. |
| 7,150,723 B2 | 12/2006 | Meguro et al. |
| 7,153,314 B2 | 12/2006 | Laufer et al. |
| 7,156,857 B2 | 1/2007 | Pasricha et al. |
| 7,169,161 B2 | 1/2007 | Bonnette et al. |
| 7,175,646 B2 | 2/2007 | Brenneman et al. |
| 7,182,771 B1 | 2/2007 | Houser et al. |
| 7,204,842 B2 | 4/2007 | Geitz |
| 7,273,451 B2 | 9/2007 | Sekine et al. |
| 7,303,531 B2 | 12/2007 | Lee et al. |
| 7,309,341 B2 | 12/2007 | Ortiz et al. |
| 7,361,180 B2 | 4/2008 | Saadat et al. |
| 7,377,897 B1 | 5/2008 | Kunkel et al. |
| 7,390,323 B2 | 6/2008 | Jang |
| 7,416,554 B2 | 8/2008 | Lam et al. |
| 7,429,264 B2 | 9/2008 | Melkent et al. |
| 7,534,247 B2 | 5/2009 | Ortiz |
| 7,591,828 B2 | 9/2009 | Ortiz |
| 7,614,999 B2 | 11/2009 | Gellman et al. |
| 7,628,768 B2 | 12/2009 | Faul et al. |
| 7,637,919 B2 | 12/2009 | Ishikawa et al. |
| 7,731,693 B2 | 6/2010 | Melsheimer |
| 7,753,872 B2 | 7/2010 | Cragg et al. |
| 7,758,565 B2 | 7/2010 | Melsheimer |
| 7,785,275 B2 | 8/2010 | Melsheimer |
| 7,828,814 B2 | 11/2010 | Brenneman et al. |
| 7,845,536 B2 | 12/2010 | Viola et al. |
| 7,914,552 B2 | 3/2011 | Shelton |
| 7,942,890 B2 | 5/2011 | D'Agostino et al. |
| 7,998,155 B2 | 8/2011 | Manzo |
| 8,016,782 B2 | 9/2011 | Brenneman et al. |
| 8,034,063 B2 | 10/2011 | Binmoeller |
| 8,088,171 B2 | 1/2012 | Brenneman |
| 8,187,289 B2 | 5/2012 | Tacchino et al. |
| 8,197,498 B2 | 6/2012 | Coleman et al. |
| 8,226,592 B2 | 7/2012 | Brenneman et al. |
| 8,236,014 B2 | 8/2012 | Brenneman et al. |
| 2001/0011170 A1 | 8/2001 | Davison et al. |
| 2002/0004663 A1 | 1/2002 | Gittings et al. |
| 2002/0183715 A1 | 12/2002 | Mantell et al. |
| 2002/0183787 A1 | 12/2002 | Wahr et al. |
| 2002/0188301 A1 | 12/2002 | Dallara et al. |
| 2003/0014063 A1 | 1/2003 | Houser et al. |
| 2003/0032975 A1 | 2/2003 | Bonutti |
| 2003/0040803 A1 | 2/2003 | Rioux et al. |
| 2003/0045893 A1 | 3/2003 | Ginn |
| 2003/0050665 A1 | 3/2003 | Ginn |
| 2003/0069533 A1 | 4/2003 | Kakutani et al. |
| 2003/0073960 A1 | 4/2003 | Adams et al. |
| 2003/0073979 A1 | 4/2003 | Naimark et al. |
| 2003/0078604 A1* | 4/2003 | Walshe ............ 606/151 |
| 2003/0088256 A1 | 5/2003 | Conston et al. |
| 2003/0093118 A1 | 5/2003 | Ho et al. |
| 2003/0109900 A1 | 6/2003 | Martinek |
| 2003/0114796 A1 | 6/2003 | Schmidt |
| 2003/0120292 A1 | 6/2003 | Park et al. |
| 2003/0163017 A1 | 8/2003 | Tam et al. |
| 2003/0236536 A1 | 12/2003 | Grigoryants et al. |
| 2004/0019322 A1 | 1/2004 | Hoffmann |
| 2004/0034371 A1 | 2/2004 | Lehman et al. |
| 2004/0049157 A1 | 3/2004 | Plishka et al. |
| 2004/0073108 A1 | 4/2004 | Saeed et al. |
| 2004/0122456 A1 | 6/2004 | Saadat et al. |
| 2004/0199087 A1 | 10/2004 | Swain et al. |
| 2004/0215220 A1 | 10/2004 | Dolan et al. |
| 2004/0236346 A1 | 11/2004 | Parker |
| 2004/0243122 A1 | 12/2004 | Auth et al. |
| 2004/0249985 A1 | 12/2004 | Mori et al. |
| 2004/0260332 A1 | 12/2004 | Dubrul et al. |
| 2005/0033327 A1 | 2/2005 | Gainor et al. |
| 2005/0043781 A1 | 2/2005 | Foley |
| 2005/0059862 A1 | 3/2005 | Phan |
| 2005/0059890 A1* | 3/2005 | Deal et al. ............ 600/433 |
| 2005/0059990 A1 | 3/2005 | Ayala et al. |
| 2005/0075654 A1 | 4/2005 | Kelleher |
| 2005/0096685 A1 | 5/2005 | Murphy et al. |
| 2005/0113868 A1 | 5/2005 | Devellian et al. |
| 2005/0187567 A1 | 8/2005 | Baker et al. |
| 2005/0228413 A1 | 10/2005 | Binmoeller et al. |
| 2005/0251159 A1 | 11/2005 | Ewers et al. |
| 2005/0251208 A1 | 11/2005 | Elmer et al. |
| 2005/0277965 A1 | 12/2005 | Brenneman et al. |
| 2005/0277981 A1 | 12/2005 | Maahs et al. |
| 2006/0015006 A1 | 1/2006 | Laurence et al. |
| 2006/0047337 A1 | 3/2006 | Brenneman |
| 2006/0062996 A1 | 3/2006 | Chien et al. |
| 2006/0111672 A1 | 5/2006 | Seward |
| 2006/0111704 A1 | 5/2006 | Brenneman et al. |
| 2006/0116697 A1 | 6/2006 | Carter et al. |
| 2006/0142703 A1 | 6/2006 | Carter et al. |
| 2006/0142790 A1 | 6/2006 | Gertner |
| 2006/0167482 A1 | 7/2006 | Swain et al. |
| 2006/0190021 A1 | 8/2006 | Hausman et al. |
| 2006/0200177 A1 | 9/2006 | Manzo |
| 2006/0217748 A1 | 9/2006 | Ortiz |
| 2006/0217762 A1 | 9/2006 | Maahs et al. |
| 2006/0224183 A1 | 10/2006 | Freudenthal |
| 2006/0258909 A1 | 11/2006 | Saadat et al. |
| 2006/0259051 A1 | 11/2006 | Nissl |
| 2006/0259074 A1 | 11/2006 | Kelleher et al. |
| 2006/0282087 A1 | 12/2006 | Binmoeller |
| 2007/0027534 A1 | 2/2007 | Bergheim et al. |
| 2007/0066863 A1 | 3/2007 | Rafiee et al. |
| 2007/0112363 A1 | 5/2007 | Adams |
| 2007/0112383 A1 | 5/2007 | Conlon et al. |
| 2007/0123840 A1 | 5/2007 | Cox |
| 2007/0123917 A1 | 5/2007 | Ortiz et al. |
| 2007/0123934 A1 | 5/2007 | Whisenant et al. |
| 2007/0135825 A1 | 6/2007 | Binmoeller |
| 2007/0179426 A1 | 8/2007 | Selden |
| 2007/0197862 A1 | 8/2007 | Deviere et al. |
| 2007/0213812 A1 | 9/2007 | Webler et al. |
| 2007/0260273 A1 | 11/2007 | Cropper et al. |
| 2007/0265656 A1 | 11/2007 | Amplatz et al. |
| 2008/0009888 A1 | 1/2008 | Ewers et al. |
| 2008/0045989 A1 | 2/2008 | Welborn |
| 2008/0065012 A1 | 3/2008 | Hebert et al. |
| 2008/0071301 A1 | 3/2008 | Matsuura et al. |
| 2008/0077180 A1 | 3/2008 | Kladakis et al. |
| 2008/0154153 A1 | 6/2008 | Heuser |
| 2008/0161645 A1 | 7/2008 | Goldwasser et al. |
| 2008/0167524 A1 | 7/2008 | Goldwasser et al. |
| 2008/0171944 A1 | 7/2008 | Brenneman et al. |
| 2008/0183080 A1 | 7/2008 | Abraham |
| 2008/0243151 A1 | 10/2008 | Binmoeller et al. |
| 2008/0249481 A1 | 10/2008 | Crainich et al. |
| 2009/0024149 A1 | 1/2009 | Saeed et al. |
| 2009/0030380 A1 | 1/2009 | Binmoeller |
| 2009/0082803 A1 | 3/2009 | Adams et al. |
| 2009/0105733 A1 | 4/2009 | Coleman et al. |
| 2009/0143713 A1 | 6/2009 | Van Dam et al. |
| 2009/0143759 A1 | 6/2009 | Van Dam et al. |
| 2009/0143760 A1 | 6/2009 | Van Dam et al. |
| 2009/0177288 A1 | 7/2009 | Wallsten |
| 2009/0227835 A1 | 9/2009 | Terliuc |

(56) References Cited

U.S. PATENT DOCUMENTS

| | | |
|---|---|---|
| 2009/0259288 A1 | 10/2009 | Wijay et al. |
| 2009/0281379 A1 | 11/2009 | Binmoeller et al. |
| 2009/0281557 A1 | 11/2009 | Sander et al. |
| 2010/0048990 A1* | 2/2010 | Bakos .................... 600/106 |
| 2010/0105983 A1 | 4/2010 | Oneda et al. |
| 2010/0130835 A1 | 5/2010 | Brenneman et al. |
| 2010/0130993 A1 | 5/2010 | Paz et al. |
| 2010/0168557 A1 | 7/2010 | Deno et al. |
| 2010/0198013 A1 | 8/2010 | Binmoeller |
| 2010/0261962 A1 | 10/2010 | Friedberg |
| 2010/0268029 A1 | 10/2010 | Phan et al. |
| 2010/0268316 A1 | 10/2010 | Brenneman et al. |
| 2011/0054381 A1 | 3/2011 | Van Dam et al. |
| 2011/0098531 A1 | 4/2011 | To |
| 2011/0112622 A1 | 5/2011 | Phan et al. |
| 2011/0137394 A1 | 6/2011 | Lunsford et al. |
| 2013/0226218 A1 | 8/2013 | Binmoeller |
| 2013/0231689 A1 | 9/2013 | Binmoeller et al. |

FOREIGN PATENT DOCUMENTS

| | | |
|---|---|---|
| EP | 1082998 A2 | 3/2001 |
| EP | 1314404 A2 | 5/2003 |
| EP | 1520526 A1 | 4/2005 |
| EP | 1520532 A2 | 4/2005 |
| EP | 1857135 A2 | 11/2007 |
| EP | 1894514 A2 | 3/2008 |
| EP | 1908421 A1 | 4/2008 |
| EP | 1824404 B1 | 8/2012 |
| GB | 2020557 A | 11/1979 |
| GB | 2269538 A | 2/1994 |
| JP | S58-35219 | 3/1983 |
| JP | 62-233168 | 10/1987 |
| JP | H05-137794 A | 6/1993 |
| JP | H05-192407 A | 8/1993 |
| JP | H05-329165 | 12/1993 |
| JP | H05-508563 | 12/1993 |
| JP | H07-096038 | 4/1995 |
| JP | 08-071158 A | 3/1996 |
| JP | 8-504940 | 5/1996 |
| JP | 8-509639 | 10/1996 |
| JP | H08-299455 A | 11/1996 |
| JP | H09-500047 A | 1/1997 |
| JP | H09-504186 A | 4/1997 |
| JP | 09-140804 A | 6/1997 |
| JP | 10-94543 | 4/1998 |
| JP | 10-155799 A | 6/1998 |
| JP | H11-512318 A | 10/1999 |
| JP | 2000-500045 A | 1/2000 |
| JP | 2000-237303 A | 9/2000 |
| JP | 2001-511658 | 8/2001 |
| JP | 2001-275947 | 10/2001 |
| JP | 2001-517524 A | 10/2001 |
| JP | 2002-119516 | 4/2002 |
| JP | 2002-524196 | 8/2002 |
| JP | 2002-534208 A | 10/2002 |
| JP | 2003-526448 | 9/2003 |
| JP | 2004-512153 | 4/2004 |
| JP | 2004-216192 | 8/2004 |
| JP | 2005-525865 | 9/2005 |
| JP | 2007514462 | 6/2007 |
| JP | 2008-534029 A | 8/2008 |
| JP | 2009500051 | 1/2009 |
| WO | WO92/20312 A1 | 11/1992 |
| WO | WO93/14688 A1 | 8/1993 |
| WO | WO 97/27898 A1 | 8/1997 |
| WO | WO 99/23952 A1 | 5/1999 |
| WO | WO 00/24449 A1 | 5/2000 |
| WO | WO 00/72909 A1 | 12/2000 |
| WO | WO 01/21247 A1 | 3/2001 |
| WO | WO 01/72367 A1 | 10/2001 |
| WO | WO01/87399 A2 | 11/2001 |
| WO | WO 03/020106 A2 | 3/2003 |
| WO | WO 03/024305 A2 | 3/2003 |
| WO | WO 03/071962 A2 | 9/2003 |
| WO | WO 2005/011463 A2 | 2/2005 |
| WO | WO 2005/096953 A1 | 10/2005 |
| WO | WO2006/115811 A1 | 11/2006 |
| WO | WO 2007/047151 A1 | 4/2007 |
| WO | WO2007115117 A1 | 10/2007 |
| WO | WO2008/005888 A2 | 1/2008 |
| WO | WO 2010/011445 A1 | 1/2010 |

OTHER PUBLICATIONS

Chopita et al.; Endoscopic gastroenteric anastomosis using magnets; Endoscopy; 37(4); pp. 313-317; Apr. 2005.

Fritscher-Ravens et al.; A through-the-scope device for suturing and tissue approximation under EUS control; Gastro Endo; 56(5); pp. 737-742; Nov. 2002.

Fritscher-Ravens et al.; Transgastric gastropexy and hiatal hernia repair for GERD under EUS control: A porcine model; Gastro Endo; 59(1); pp. 89-95; Jan. 2004.

Kahaleh et al.; Interventional EUS-guided cholangiography: evaluation of a technique in evolution; Gastrointestinal Endoscopy; 64(1); pp. 52-59; Jul. 2006.

Kwan et al.; EUS-guided cholecystenterostomy: a new technique; Gastrointestinal Endoscopy; 66(3); pp. 582-586; Sep. 2007.

Swain et al.; Knot tying at flexible endoscopy; gastro endo; 40(6); pp. 722-729; Nov. 1994.

Phan et al.; U.S. Appl. No. 13/364,265 entitled "Apparatus and Method for Deploying Stent Across Adjacent Tissue Layers," filed Feb. 1, 2012.

Lepulu et al.; U.S. Appl. No. 13/281,410 entitled "Apparatus and Method for Penetrating and Enlarging Adjacent Tissue Layers," filed Oct. 25, 2011.

Lepulu et al.; U.S. Appl. No. 13/363,297 entitled "Apparatus and Method for Penetrating and Enlarging Adjacent Tissue Layers," filed Jan. 31, 2012.

Maisin et al.; Patency of endoscopic cystoduodenostomy maintained by a Z stent; Gastrointestinal Endoscopy; 40(6); pp. 765-768; Nov. 1994.

Brown et al.; U.S. Appl. No. 13/871,978 entitled "Methods and devices for access across adjacent tissue layers," filed Apr. 26, 2013.

Sander et al.; U.S. Appl. No. 13/892,958 entitled "Tissue Anchor for Securing Tissue Layers," filed May 13, 2013.

Blum et al.; Endoluminal stent-grafts for infrarenal abdominal aortic aneurysms; NEJM; 336(1); pp. 13-20; Jan. 2, 1996.

Spillner et al.; Initial clainical experiences with endovascular stent-grafts for treatment of infrarenal abdominal aortic aneurysm (in German w/ English Summary); Zentralbi Chir.; 121(9); pp. 727-733; 1996 (year of pub. sufficiently earlier than effective US filing date and any foreign priority date).

Binmoeller et al.; Silicone-covered expanadable metallic stents in the esophagus: an experimental study; Endoscopy; 24; pp. 416-420; Jun. 1992.

Davies et al.; Percutaneous cystogastrostomy with a new catheter for drainage of pancreatic pseudocysts and fluid collections; Cardiovascular and Interventional Radiology; 19; pp. 128-131; Mar. 1996.

Schaer et al.; Treatment of malignant esophageal obstruction with silicon-coated metallic self-expanding stents; Gastrointestinal Endoscopy; 38(1); pp. 7-11; Jan. 1992.

Binmoeller et al.; U.S. Appl. No. 14/186,994 entitled "Devices and methods for forming an anastomosis," filed Feb. 21, 2014.

* cited by examiner

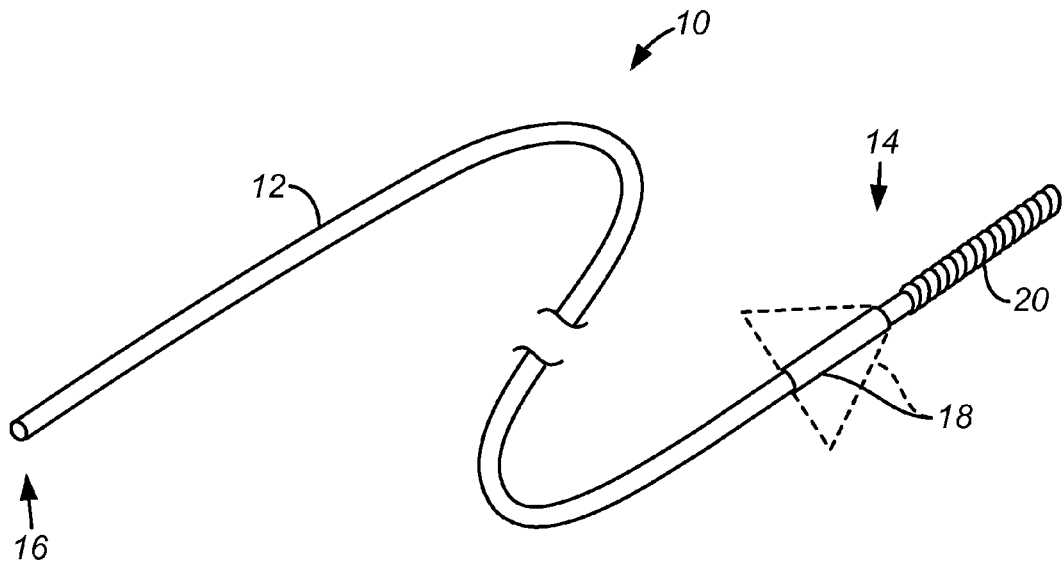
FIG. 1
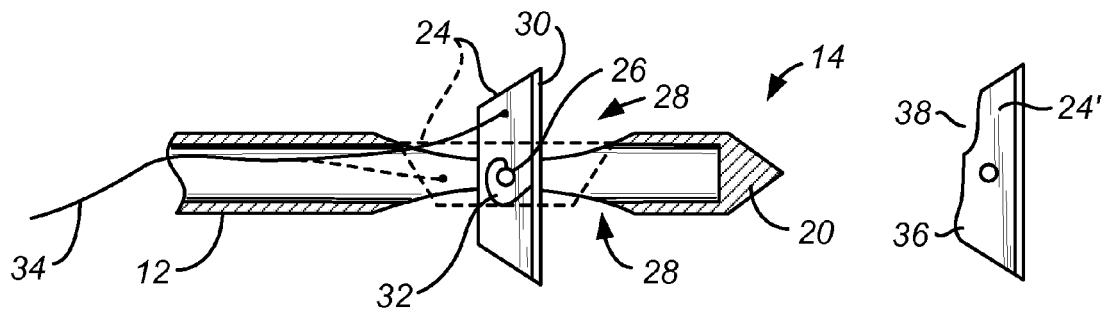
FIG. 2  FIG. 2A
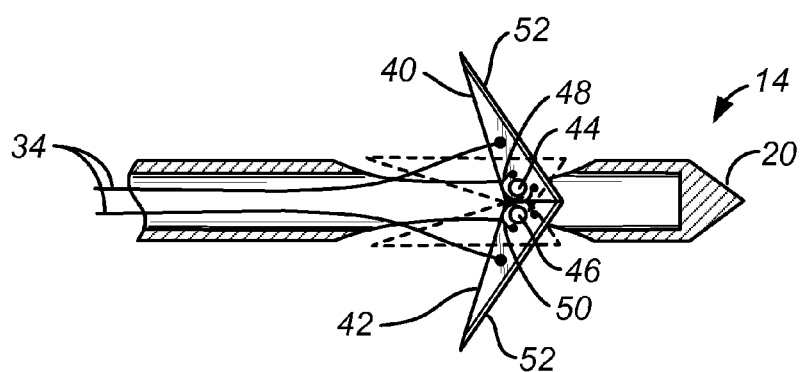
FIG. 3

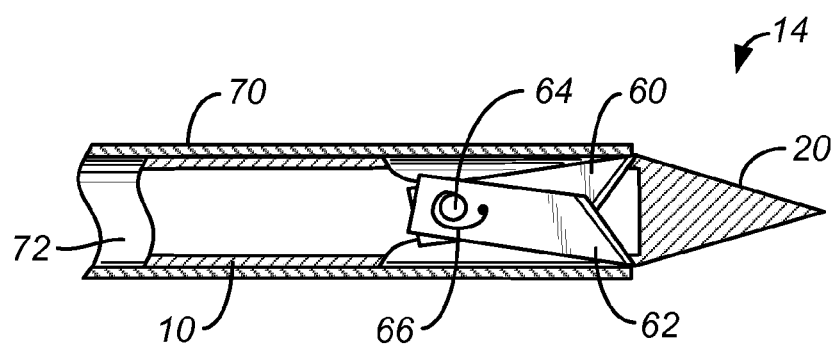
FIG. 4A
FIG. 4B
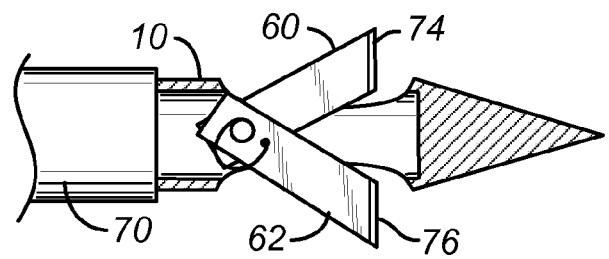
FIG. 5A
FIG. 5B
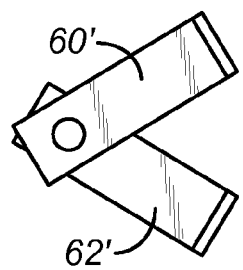
FIG. 5C
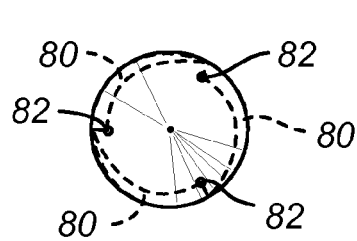
FIG. 6A
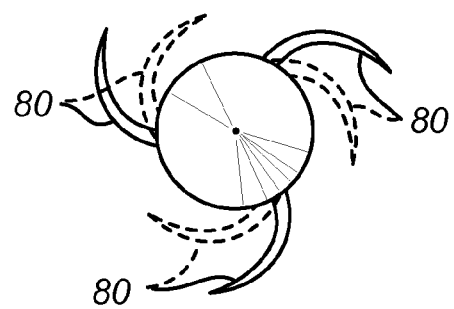
FIG. 6B

SYSTEM AND METHOD FOR DELIVERING EXPANDING TROCAR THROUGH A SHEATH

CROSS-REFERENCES TO RELATED APPLICATIONS

This application claims the benefit of priority of U.S. Provisional Patent Application No. 61/171,228, filed on Apr. 21, 2009, which is incorporated herein by reference.

BACKGROUND OF THE INVENTION

1. Field of the Invention

The present invention relates generally to medical apparatus and methods. In particular, the present invention relates to a penetration device, such as a trocar, having the ability to expand the size of a tissue penetration as the tool is advanced.

A number of endoscopic and other intraluminal procedures require penetration from one body lumen into an adjacent body lumen. For example, a number of procedures may be performed by entering the gastrointestinal (GI) tract, particularly the stomach, duodenum, small intestine and large intestine, and passing tools from the GI tract into adjacent organs, ducts, cavities and structures, such as the bile duct, the pancreatic duct, the gallbladder, urinary tract, a cyst or pseudocyst, abscess, and the like. Since the endoscopes and other endoscopic access tools are generally small with narrow working channels, typically 2 to 7 millimeters in diameter, any penetrating tools which are advanced through such working channels will necessarily be small and provide for only small tissue penetrations.

Depending on the procedure being performed, it is often desirable to place a catheter, a stent, a drainage tube, a fiducial marker implant, an electrode or a like second diagnostic or therapeutic device, through the penetrations that have been formed. Often, placement of such tools and implants requires a relatively large diameter hole to allow subsequent passage of the second device. In many cases the desired diameter of the second device is larger than the maximum diameter of the penetrating member and the insertion of the second device is often difficult. Commonly, the lumen walls include muscle layers and significant force is required to advance the catheter from one lumen to the next. Such advancement can be more difficult and may fail if the size of the penetrating element is increased in order to provide a larger penetration.

For these reasons, it would be desirable to provide trocars or other tissue-penetrating devices which can be used intraluminally to penetrate from one body lumen into an adjacent lumen where the size of the penetration can easily be enlarged. In particular, it would be desirable to provide such tools and methods where a relatively low force is needed to advance the tool through the tissue while still achieving a relatively large penetration. Such tools and methods should be compatible with standard endoscopes and other sheaths which can be used to access a target location in the gastrointestinal tract or other body lumen. At least some of these objectives will be met by the inventions described hereinbelow.

2. Description of the Background Art

Trocars and other medical access devices having deployable cutting blades are described in U.S. Pat. Nos. 5,372,588; 5,620,456; 6,402,770; 7,429,264; and US 2008/0045989. Other disclosures of interest are found in U.S. Pat. Nos. 5,224,945; 5,697,944; 6,371,964; 7,303,531; and US 2006/0190021.

BRIEF SUMMARY OF THE INVENTION

The present invention provides improved trocars and other tissue-penetrating devices which can be used with endoscopes and other viewing scopes and sheaths. The trocars can be advanced from a working channel or other lumen or passage of the sheath and penetrated through an adjacent luminal wall and, typically, further into and through the wall of an adjacent body structure or organ. Thus, the trocars are particularly useful for providing intraluminal access from one body lumen or cavity into an adjacent body lumen or cavity. The trocars will most often be used for forming penetrations and passages from a gastrointestinal structure, such as the esophagus, the stomach, the duodenum, the small intestine, and the large intestine, into an adjacent structure or organ, such as the bile duct, the pancreatic duct, the gallbladder, the urinary tract, a cyst or pseudocyst, an abscess, and the like. The trocars of the present invention are useful in any medical procedure where an elongate, flexible tool is advanced through an access sheath to a remote location in order to penetrate tissue.

Trocars according to the present invention are intended for use with a catheter, endoscope, or delivery sheath having a working channel or other lumen. Such trocars usually comprise an elongate body which can be advanced through the sheath working channel or lumen, typically having a flexible body with a stiffness typical for standard endoscopic biopsy needles. At least one blade will be disposed near a distal end of the elongate body where the blade is biased to open from a radially retracted configuration to a radially extended configuration. In particular, the blade will be radially retracted when the distal end of the elongate body is disposed within the sheath lumen, and the blade will open radially when the distal end is advanced distally beyond the end of the sheath lumen. Usually, the blade(s) will be adapted to close radially in response to being drawn back into the sheath lumen. In this way, the trocar body can have a relatively small width or diameter, typically in the range from 0.4 mm to 5 mm, while the extended blades can significantly increase the size of the tissue penetration which is formed when the distal end of the trocar is advanced through tissue. Moreover, as the blade is biased to open as the distal end of the trocar is extended beyond the working channel of the sheath, there is no need for the physician to separately actuate the blade and instead the larger cutting size is automatically provided as the penetration is being performed.

Usually, at least a portion of the forward edge or surface of the blade will be sharpened or otherwise adapted so that it can penetrate tissue. Typically, conventional honing or other physical modification of the blade will be sufficient to provide the cutting surface. Alternatively, electrodes or other electrosurgical carriers, wires, metalized surfaces, or the like, may be provided on the blade in order to enhance the cutting effect when connected to a suitable electrosurgical power supply. In contrast, the trailing or proximal side of the blade will usually be blunt or atraumatic in order to avoid accidental cutting or tissue trauma when the trocar is pulled back. A blunt trailing edge is further desirable when the blade is configured to close as it is drawn proximally to engage a leading edge of the working channel of the endoscope or sheath.

In other embodiments, the blade can be configured to be actively closed by the physician after the tissue penetration is complete. For example, a tether or other structure for pulling the blade back to close the blade against the bias may be provided.

In most embodiments, the elongate body of the trocar will also have a fixed tissue-penetrating element at its distal tip to permit or facilitate advancement through tissue. The tissue-penetrating tip may comprise a sharpened tip, a chamfered tip, an electrosurgical tip, or any other common tip or modification which allows the body to be advanced forwardly to penetrate tissue. In other embodiments, however, it may be possible to provide a body having a blunt or atraumatic tip where the deployed blade provides the entire cutting surface for the trocar.

In some embodiments, the trocar will include only a single blade which is pivotally mounted so that opposite ends of the blade rotate to open from opposite sides of the elongate body. Such embodiments may be biased using a coiled spring disposed about an axis or pivot point of the blade. Such rotating single blades can be used together with a tether for tensioning the blade to rotate and collapse or otherwise close the blade back into the elongate body. Alternatively, the blade and sheath can be configured such that drawing the trocar proximally back into the sheath automatically retracts the blade.

In other embodiments, the trocar may comprise at least two biased blades attached to a single pivot point to open in a scissors-like pattern where each of the blades has a sharpened distal edge to cut tissue as the elongate body is advanced. In still other embodiments, two biased blades may be attached to pivot points on opposite sides of the elongate body where the blades are parallel to each other when retracted within the elongate body. In further embodiments, two blades may be attached at axially spaced-apart locations on the elongate body and/or in rotationally spaced apart locations. In addition to planar blades, the blades may comprise pre-shaped wires or other shape-memory components which radially expand outwardly when released from constraint. In such cases, the wires are typically not pivoted in any way. In still other embodiments, the blades may be conformed circumferentially over the surface of the elongate body and attached with an axial line hinge with springs to radially open or unfold the blades.

The present invention further provides methods for accessing internal body organs. The methods of the present invention comprise introducing a delivery sheath through the working channel of an endoscope to a location adjacent to a target location on a wall of an organ or lumen. A trocar is then advanced from a lumen in the delivery sheath so that the trocar penetrates the organ or lumen wall at the target location. As the trocar is advanced, a blade is released from constraint so that the blade opens radially as the trocar exits the lumen. The released, expanded blade may thus enlarge the penetration which was made by the distal tip of the trocar as it was advanced. In many cases, the endoscope, viewing scope, or other delivery sheath from which the trocar was advanced will be introduced through a natural body orifice, such as the mouth, anus, ureter, and/or vagina and cervix, allowing for the performance of a natural-orifice translumenal endoscopic surgery (NOTES) which avoids the need to form a percutaneous tissue penetration. In addition, translumenal interventional endoscopy procedures can be accomplished including transoral or transanal access of a cyst, pseudocyst or abscess for drainage into the GI tract, transoral or transanal access of the gallbladder, bile duct and pancreatic duct for drainage into the GI tract, transoral access of the heart from the esophagus for delivery of drugs, placement of electrodes, and ablation of tissue, transoral access of the pancreas, gallbladder, kidneys, liver, spleen and any other organs or structure adjacent to the GI lumen to deliver fiducial markers, drugs, and tissue ablation from the GI tract.

BRIEF DESCRIPTION OF THE DRAWINGS

FIG. 1 illustrates a trocar having an extendable blade constructed in accordance with the principles of the present invention.

FIGS. 2 and 2A illustrate a first particular construction of the actuable blade of the trocar of the present invention.

FIG. 3 illustrates a second particular embodiment of an actuable blade constructed in accordance with the principles of the present invention.

FIGS. 4A and 4B illustrate yet another embodiment of the actuable blade mechanism of the trocars of the present invention, where FIG. 4A is a cross-sectional view of a distal section of the trocar and FIG. 4B is an end view of the distal section.

FIGS. 5A-5C are similar to FIGS. 4A and 4B, except that the blade structure has been actuated by advancing the trocar out the distal end of a constraining sheath.

FIGS. 6A and 6B illustrate a blade assembly where three blades are axially hinged in order to open in a radial or petal pattern.

DETAILED DESCRIPTION OF THE INVENTION

Figure 7A:
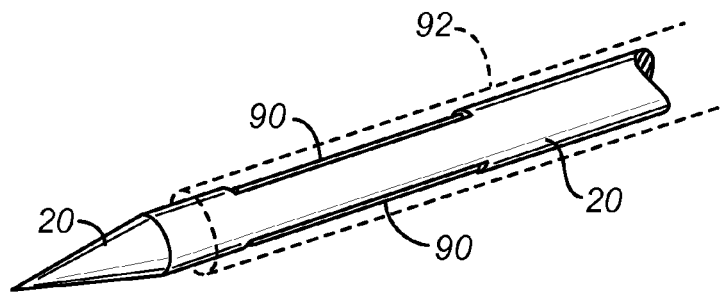
FIGS. 7A and 7B illustrate a deformable wire blade structure on a trocar according to the present invention.

Referring to FIG. 1, a trocar 10 constructed in accordance with the principles of the present invention comprises an elongate body 12 having a distal end 14 and a proximal end 16. An actuable blade structure 18 is disposed near the distal end 14 of elongate body 12, where the blade is shown in a radially expanded configuration in broken line.

The length and dimensions of the elongate body 12 will depend on the intended use of the trocar. Typically for gastrointestinal procedures, elongate body 12 of the trocar will be sized to be introduced through an endoscope and will have a length in the range from 50 cm to 500 cm and a width or diameter in the range from 0.4 mm to 5 mm. The elongate body may be a solid wire or have a hollow structure with an axial passage or lumen. The body may be formed from polymers, such as polytetrafluoroethylene (PTFE), nylon, poly (ether ether ketone) (PEEK) or polyethyleneterephthalate (PET), or metals, such as stainless steel, elgiloy, or nitinol. In certain instances, it may be desirable to reinforce the body with braid, helical wires, or other conventional components. In other cases, the body may be formed from different materials over its proximal length and its distal length. For example, the proximal length may be formed from metal hypotube or wire while the distal, more flexible portion is formed from a polymer tube, optionally a reinforced polymer tube. In other embodiments, the elongate body 12 may be straight and relatively rigid over its entire length.

Figure 9A:
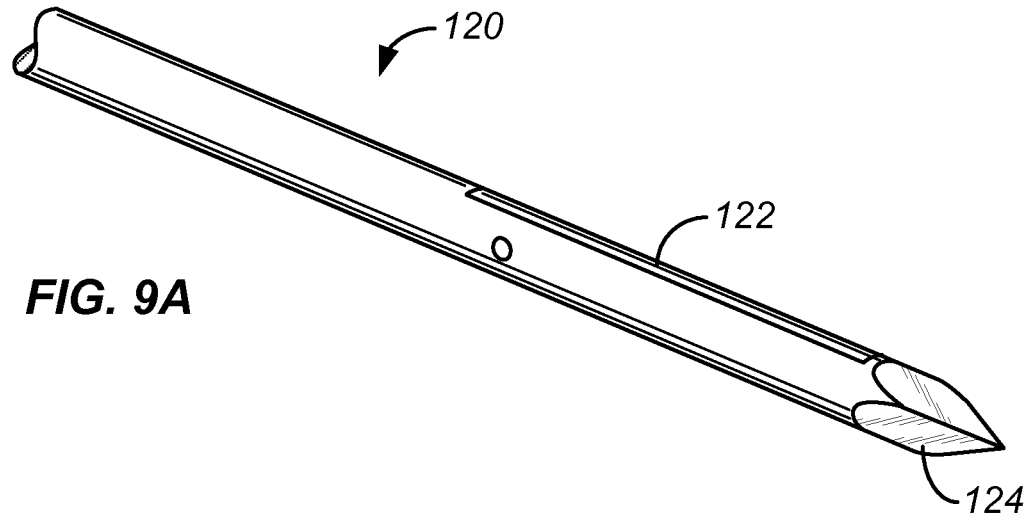
FIGS. 9A to 9C illustrate a single asymmetric blade embodiment of the trocar of the present invention.
Figure 9B:
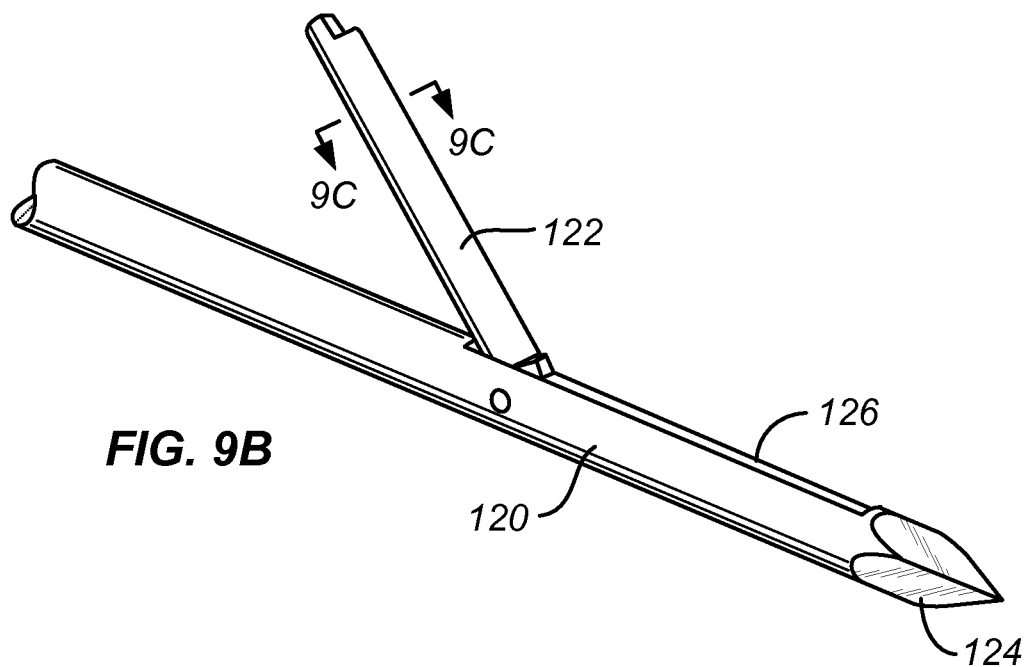

The elongate body 12 will usually have a tissue-penetrating tip 20 at its distal end, where the tip may be conical, chamfered, electrosurgical, or be provided in any conventional form for a trocar. For example, the tip might have a multi-faceted face with sharpened edges for penetrating, as is commonly employed with tissue-penetrating trocars (as shown in FIGS. 9A and 9B).

Referring now to FIG. 2, a first embodiment of the blade assembly 18 will be described. A single blade 24 is mounted within the elongate body 12 on a pivot 26. A pair of opposed windows 28 allow the blade to rotate or pivot between an axially aligned configuration, as shown in broken line, where the blade is fully refracted within the peripheral envelope of the trocar, and a radially extended configuration shown in full line where a leading, cutting edge 30 of the blade is disposed toward the distal end 14. The blade is biased by a coil spring 32 (a leaf or other spring could also be used) which is attached at one end to the blade and the other end to the fixed pivot so that, in the absence of constraint, the blade will open to its extended configuration as shown in full line. Thus, when constrained within a sheath or working channel or other lumen of an endoscope, the blade will be held in its retracted or constrained configuration, as shown in broken line. When advanced from the sheath or working channel, however, the spring 32 will automatically open the blade so that the cutting edge 30 is exposed to the tissue as the trocar is advanced. It is also possible for the spring to only partially open the blade once the trocar is advanced from the sheath, the initial tissue interference of cutting edge 30 then causing the blade to fully open and penetrate through the tissue layers. After use, the blade can be closed by pulling proximally on a tether 34 to close the blade down to its retracted (broken line) configuration.

Alternately the blade and constraining sheath can be configured such that proximal movement of the trocar into the constraining catheter results in automatic retraction of the blade. In this instance, as shown in FIG. 2A, the lower rear edge of the blade 24' has a protrusion 36 that contacts the constraining catheter as the trocar is moved proximally relative to the sheath, thus rotating the blade against the spring force into the refracted configuration. A relief or cut out 38 may also be formed on the upper rear edge of blade 24' to prevent the rear edge of the blade from interfering with the catheter as it is retracted. Alternatively, the upper rear edge of the blade may be sharpened (in addition to or in place of the cut out 38). Drawing the trocar into the constraining catheter or sheath causes the protrusion 36 to contact the leading edge of the constraining catheter/sheath rotating the blade counterclockwise (as seen in FIG. 2). The sharpened edge will cut any tissue that may be between it and the trocar, allowing it to retract fully.

Referring now to FIG. 3, a further embodiment of the blade structure 18 includes a pair of opposed blades 40 and 42. Each of the blades 40, 42 is mounted on a pivot 44 and 46, respectively, and includes a spring 48 and 50 which will open the blade from the retracted or constrained configuration shown in broken line to the extended configuration shown in full line. Each blade has a cutting edge 52 which is exposed to tissue as the trocar 10 is advanced distally. The blades each have a tether 34 to permit the blades to be retracted after use. Alternately these blades can be configured such that the tip of the retracted blade is positioned distal to the pivot, requiring a proximal rotation of the blade into the extended orientation. In this configuration the trocar can automatically retract as the trocar is pulled distally into the restraining catheter.

In the embodiments of both FIGS. 2 and 3, the blades will not automatically retract as the trocar 10 is pulled back into a sheath or endoscope. Thus the tethers are needed to retract the blades prior to pulling the trocars back into the sheath. In other embodiments, however, as described below, the blades will automatically retract as the trocar is pulled back into a sheath. The first such structure is illustrated in FIGS. 2A, 4A/B and 5A/B.

The trocar 10 of FIGS. 4A and 4B includes blades 60 and 62 mounted on a single common pivot 64. Each blade has a coil spring 66 attached to the blade and pivot in order to open the blade, as shown in FIGS. 5A and 5B, in the absence of constraint. As shown in FIGS. 4A and 4B, the blades 60 and 62 are constrained within a sheath 70 having a passage or channel 72 through which the trocar can be advanced or retracted. So long as the blades 60 and 62 of the trocar 10 are within the lumen 72 of the sheath 70, the blades remain constrained as shown in FIGS. 4A and 4B. By advancing the distal end 14 of the trocar further from the distal opening of the sheath 70, as shown in FIGS. 5A and 5B, the blades 60 and 62 will automatically open under the spring bias so that leading cutting edges 74 and 76 are exposed to tissue as the trocar is advanced therethrough. In this embodiment, the blades will automatically retract and close as the trocar 10 is pulled back within the sheath 70 since the distal end of the sheath will engage the back sides of the blades to close the blades as they reenter the sheath. Leading cutting edges 74 and 76 are shown being perpendicular to the axis of the trocar, however it may be desirable for cutting edges to be tapered or angled proximally to enhance the ease of the puncture. In this case, the lateral most tip of the open blade is positioned proximal to the inboard tip of the blade as shown in FIG. 5C (blades 60' and 62').

A variety of other biased blade constructions may be employed. For example, as shown in FIGS. 6A and 6B, multiple blades 80 may be mounted on axially aligned pivots 82 so the blades open or unfold in a petal-like manner as they rotate about the longitudinal axes of the pivots 82. Springs may be provided in order to unfold the blades 80 and tethers may be provided to close the blades.

Figure 7B:
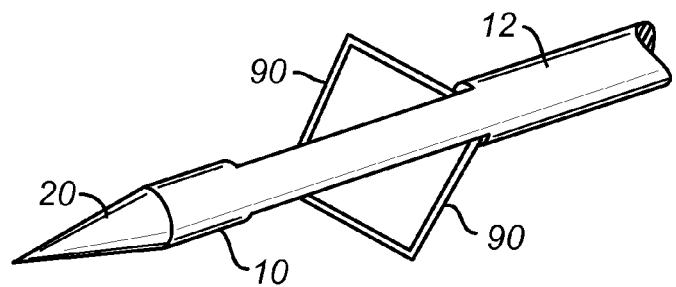

In still further embodiments, the blades may comprise deformable structures rather than pivoted structures. For example, as shown in FIGS. 7A and 7B, a plurality of wire blades 90 will be provided on the elongate body 12 of the trocar 10. The blades may be formed from a resilient material, such as spring stainless steel, Nitinol, or other shape memory materials, and may be heat set to have the open, cutting configuration as shown in FIG. 7B. Thus, in the absence of constraint, the blades will "spring" to their extended cutting configuration. The blades may be retracted by drawing them into the constraining sheath 92, shown in broken line in FIG. 7A.

Figure 8A:
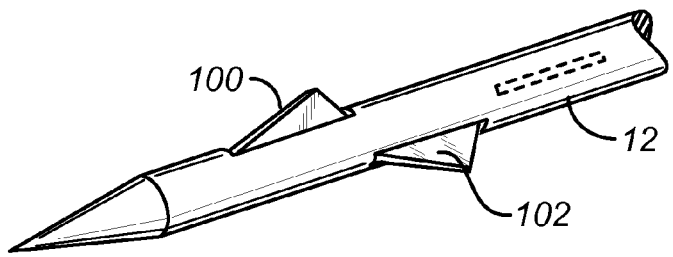
FIGS. 8A and 8B illustrate axially and radially spaced-apart blades on a trocar in accordance with the principles of the present invention.
Figure 8B:
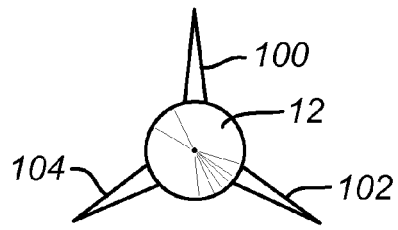

Referring to FIGS. 8A and 8B, a plurality of blades may be provided in a variety of configurations. As seen in FIG. 8A, blades 100 and 102 may be axially spaced-apart over the elongate body 12, while as shown in FIG. 8B, the blades may be radially spaced-apart in configurations other than 180° opposition.

Figure 9C:
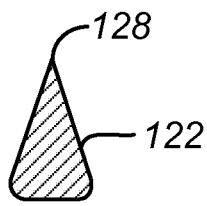

A trocar 120 having a single, asymmetrically attached blade 122 is illustrated in FIGS. 9A-9C. The trocar 120 has a faceted tip 124 and a trough or recess 126 which receives the pivotally mounted blade 122. The blade 122 will be biased, typically by a resilient structure such as a coil or leaf spring (not shown), to open at an angle greater than 90° so that the blade is "swept back" as it is held by engaging the rear edge of the recess 126. The blade 122 has a honed edge 128, as best seen in FIG. 9C so that it will cut a wide incision through tissue as the trocar is advanced. The blade 122 may be closed by refraction back into the lumen or passage of the deployment sheath.

Figure 10A:
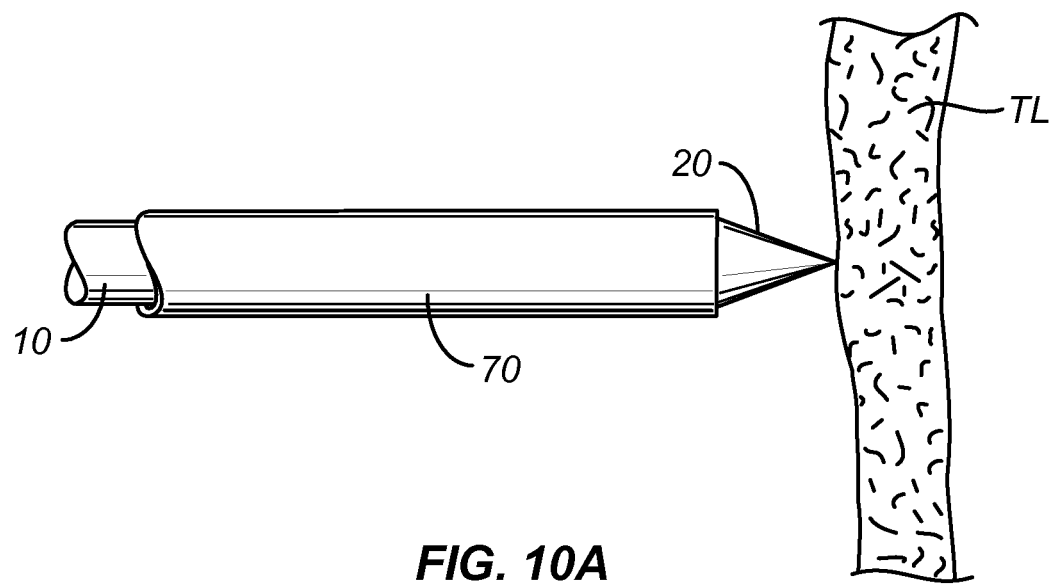
FIGS. 10A-10D illustrate use of the trocar of FIGS. 4A/B and 5A/B for penetrating a tissue wall in accordance with the principles of the present invention.
Figure 10B:
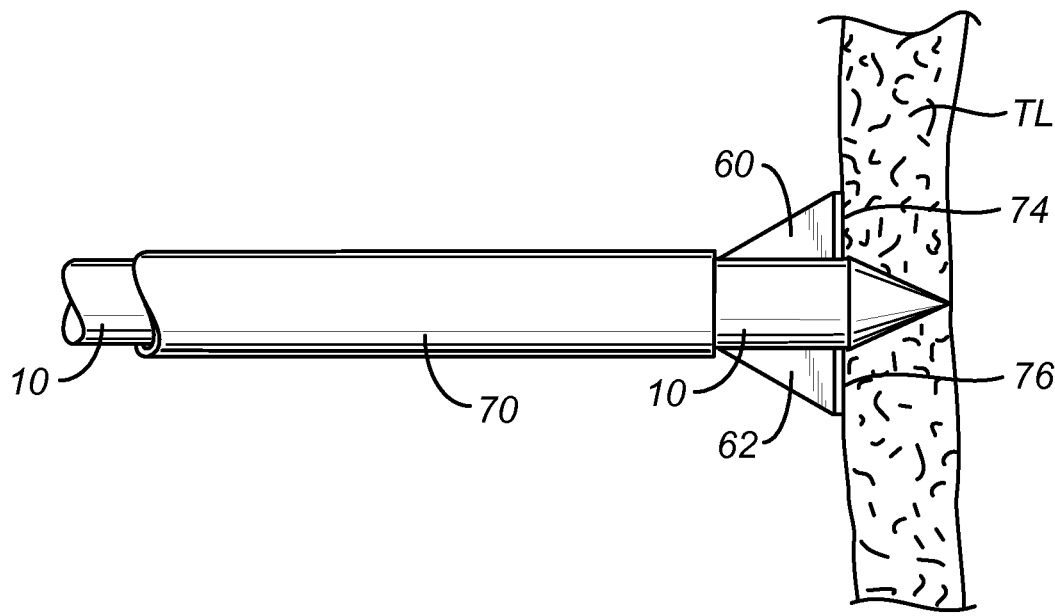
Figure 10C:
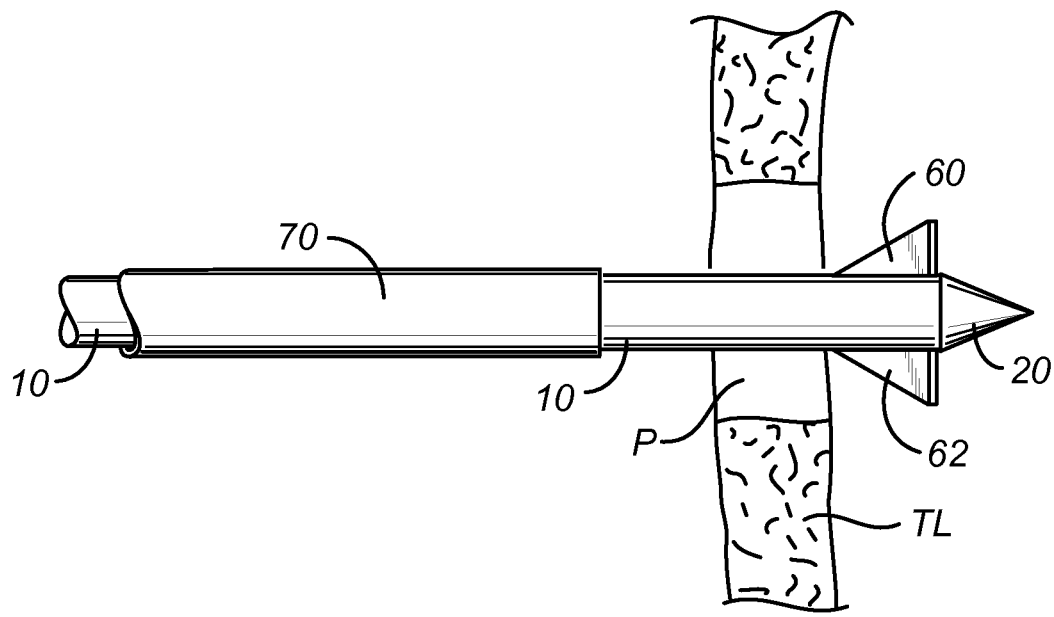
Figure 10D:
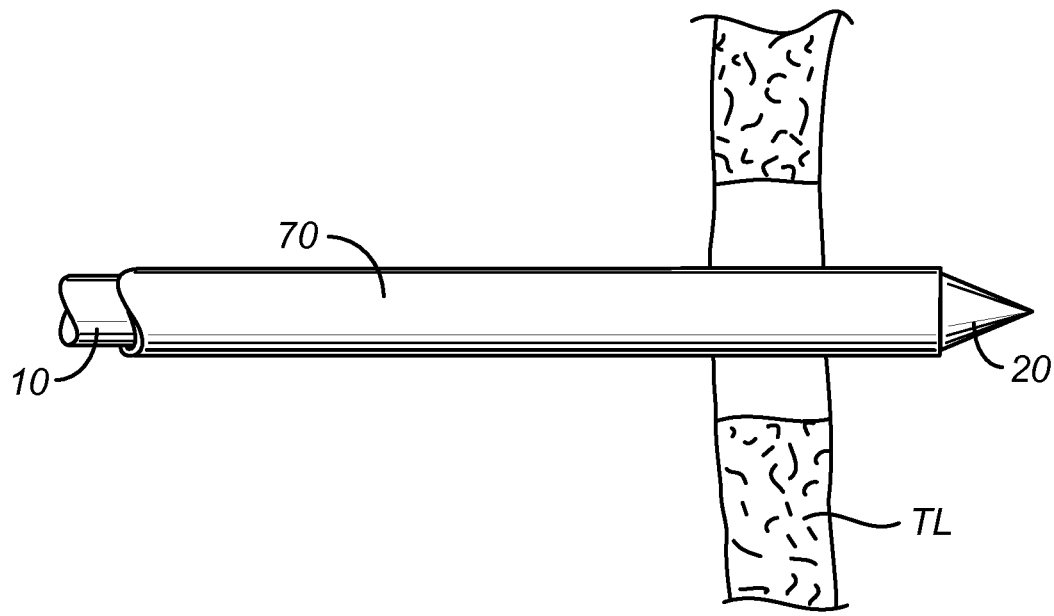

Referring now to FIGS. 10A-10D, use of the trocar 10 of FIGS. 4A/4B and 5A/5B for penetrating a tissue layer TL will be described. Initially, trocar 10 is advanced to the tissue layer with the blades retracted within sheath 70 and the penetrating tip 20 of the trocar engaged against the tissue layer. The blades 60 and 62 extend radially as the trocar 10 is advanced from the sheath 70, as shown in FIG. 10B. The penetrating tip 20 of the trocar will have entered the tissue as the blades extend and the cutting edges 74 and 76 engage the tissue. The trocar continues to be advanced through the tissue layer TL until it passes out the other side, as shown in FIG. 10C. It can be seen that the penetration P formed has a width which is much greater than would have been obtained using the trocar 10 without the blades 60 and 62. Before withdrawing the sheath 70, it can be advanced over the sheath to close the blades, as shown in FIG. 10D, and the sheath can be pulled back through the penetration P without exposing the blades unintentionally.

While the above is a complete description of the preferred embodiments of the invention, various alternatives, modifications, and equivalents may be used. Therefore, the above description should not be taken as limiting the scope of the invention which is defined by the appended claims.

What is claimed is:

1. A method for accessing an internal body organ, said method comprising:
    introducing an endoscope to a location adjacent to a wall of the organ; and
    advancing a trocar from a lumen in the endoscope, wherein the trocar penetrates the wall of the organ to access a cyst, pseudocyst, abscess, gall bladder, urinary bladder, bile duct, or pancreatic duct;
    wherein advancing the trocar releases a blade having a sharpened distal edge from constraint within the lumen so that the blade opens radially to an angle greater than 90 degrees from an elongate body of the trocar as the trocar exits the lumen such that the sharpened distal edge of the blade enlarges the penetration made by a distal tip of the trocar.

2. The method as in claim 1, wherein the endoscope is introduced through a natural body orifice, wherein the endoscope is flexible.

3. The method as in claim 2, wherein the endoscope is introduced transorally or transnasally into a GI tract to access the cyst, pseudocyst, or abscess.

4. The method as in claim 2, wherein the endoscope is introduced transorally or transnasally into a GI tract to access the gall bladder or the urinary bladder.

5. The method as in claim 1, wherein the lumen comprises a working channel of the endoscope.

6. The method as in claim 1, wherein the trocar has a tissue-penetrating tip and forms the penetration as it is advanced through the organ wall.

7. The method as in claim 1, wherein the blade is biased to spring open as the constraint is removed.

8. The method as in claim 1, wherein a single blade opens.

9. The method as in claim 2, wherein the endoscope is introduced transorally or transnasally into a GI tract to access the bile duct or pancreatic duct.

10. The method as in claim 2, wherein the endoscope is introduced transorally or transnasally into a GI tract to access an organ or structure in an abdominal, pelvic or thoracic cavity adjacent to the GI tract.

11. The method as in claim 1, wherein the endoscope comprises a catheter with a length from 20 cm to 500 cm and a diameter from 1 mm to 5 mm.

12. The method as in claim 1, wherein the blade is contained within the elongate body of the trocar in a closed position.

13. The method as in claim 1, wherein the blade opening radially comprises rotating the blade about a pivot point relative to the elongate body of the trocar.

* * * * *